United States Patent [19]

Oka et al.

[11] Patent Number: 5,298,165
[45] Date of Patent: Mar. 29, 1994

[54] METHOD FOR REMOVING LEUKOCYTES AND A FILTER SYSTEM FOR REMOVING THE SAME

[75] Inventors: Shin-Ichiroh Oka; Takao Nishimura, both of Oita, Japan

[73] Assignee: Asahi Medical Co., Ltd., Tokyo, Japan

[21] Appl. No.: 838,268

[22] PCT Filed: Sep. 25, 1991

[86] PCT No.: PCT/JP91/01277
§ 371 Date: Mar. 13, 1992
§ 102(e) Date: Mar. 13, 1992

[87] PCT Pub. No.: WO92/04906
PCT Pub. Date: Apr. 2, 1992

[30] Foreign Application Priority Data

Sep. 25, 1990 [JP] Japan ................. 2-251998

[51] Int. Cl.$^5$ ............. B01D 27/02; B01D 36/02; B01D 39/00; B01D 21/26
[52] U.S. Cl. .................. 210/645; 210/335; 210/491; 210/505; 210/782; 210/787; 210/806
[58] Field of Search ............ 210/645, 767, 806, 335, 210/489, 491, 492, 503, 504, 505, 507, 508, 295, 509, 782, 787

[56] References Cited

U.S. PATENT DOCUMENTS

| | | | |
|---|---|---|---|
| 4,416,777 | 11/1983 | Kuroda et al. | 210/504 |
| 4,701,267 | 10/1987 | Watanabe et al. | 210/806 |
| 4,925,572 | 5/1990 | Pall | 210/767 |
| 4,936,998 | 6/1990 | Nishimura et al. | 210/767 |

FOREIGN PATENT DOCUMENTS 1-236064 9/1989 Japan.

*Primary Examiner*—Robert A. Dawson
*Assistant Examiner*—Sun Uk Kim

[57] ABSTRACT

A method for removing leukocytes from a leukocyte-containing blood product, include subjecting a leukocyte-containing blood product to a first stage leukocyte-removing treatment to remove at least 60% of all leukocytes contained in the leukocyte-containing blood product, thereby obtaining a leukocyte-depleted blood product, and passing the leukocyte-depleted blood product through a microfilter element to perform a second stage leukocyte-removing treatment, the microfilter element having a non-woven or a woven fabric including fibers having an average diameter of from 0.3 to 1.6 μm. A filter system for removing leukocytes from a leukocyte-containing blood product, to includes a first filter element for the first stage and a second filter element for the second stage, wherein the first filter element communicates with the second filter element and is positioned upstream of the second filter element with respect to a direction in which a leukocyte-containing blood product is to be flowed. By the method and filter system of the present invention, leukocytes can effectively be removed from a leukocyte-containing blood product to a level of a leukocyte residual ratio of $10^{-4}$ or less and, in addition, a miniaturization of leukocyte-removing filters can be attained.

9 Claims, No Drawings

METHOD FOR REMOVING LEUKOCYTES AND A FILTER SYSTEM FOR REMOVING THE SAME

TECHNICAL FIELD

The present invention relates to a method for removing leukocytes and a filter system for removing the same. More particularly, the present invention is concerned with a method for removing leukocytes from a leukocyte-containing blood product, such as whole blood, a red cell product and a platelet product, and is also concerned with a filter system for removing leukocytes, which is useful for practicing the above-mentioned method.

BACKGROUND ART

In recent years, in the field of blood transfusion, a leukocyte-free blood transfusion in which leukocytes are removed from a blood product before transfusion is increasingly employed. This is because it has become apparent that side effects of transfusion, such as headache, nausea, chills and non-hemolytic feverish reaction, and side effects more serious to a recipient, such as allosensitization, post-transfusion GVHD (graft versus host disease) and viral infection, are mainly caused by leukocytes contained in a blood product employed in transfusion.

It is known that the number of leukocytes injected into a recipient at one transfusion must be limited to about 100,000,000 or less in order to avoid relatively slight side effects, such as headache, nausea, chills and fever. For meeting this requirement, leukocytes must be removed from a blood product to a level of $10^{-1}$ to $10^{-2}$ or less in terms of a leukocyte residual ratio. With respect to allosensitization, it now attracts the greatest attention in the art of blood transfusion, and it is one of the side effects, prevention of which is most desired. For preventing this serious side effect, it is believed that the number of leukocytes injected into a recipient at one transfusion must be limited to 5,000,000 or less, preferably 1,000,000 or less. For meeting this requirement, leukocytes must be removed from a blood product to a level of $10^{-4}$ or less in terms of a leukocyte residual ratio. With respect to post-transfusion GVHD and viral infection, no generally accepted standards for leukocyte-removal have been established. However, it is expected that infection with a virus, which is believed to exist only in leukocytes, such as cytomegalo virus, adult T cell leukemia virus and post-transfusion GVHD, could be prevented by removing leukocytes to a level of $10^{-4}$ to $10^{-6}$ or less in terms of a leukocyte residual ratio. Further, it is also expected that the probability of infection with a virus, which is believed to exist in both leukocytes and plasma, such as HIV, can be decreased by removing leukocytes.

The methods for removing leukocytes from a blood product can generally be classified into two methods. One is a method in which leukocytes are separated by a centrifuge, taking advantage of a specific gravity difference therebetween. The other is a filtering method in which leukocytes are removed by a filter comprising a fiber material or a spongy structure as a filter medium. In particular, a filtering method in which leukocytes are adsorption-removed by a non-woven fabric is widely employed due to the advantages of high capability to remove leukocytes, ease in handling and low cost.

Most of the conventional leukocyte-removing filters comprising a non-woven fabric are composed of two functionally different filter elements, i.e., a prefilter for removing aggregates, which has an average fiber diameter of from about 3 to 30 μm and a relatively large pore size, and a main filter as an essential element for removing leukocytes, which is comprised of fibers having an average diameter of from about 1.7 to 3 μm. With respect to the above-mentioned prefilter, it is preferably comprised of a plurality of layers in which the average fiber diameters and the pore sizes of the layers are decreased in the direction from a blood inlet toward a blood outlet (Japanese Patent Application Publication Specification No. 2-13588 and WO 89/03717). Aggregates are formed by aggregation of denatured blood components comprising fibrinogen, fibrin, denatured protein, nucleic acid and/or fat globule, or by aggregation of cellular components, such as leukocytes and platelets. The aggregates are highly sticky, and their sizes have a very broad distribution, i.e., from several microns to 100 μm, sometimes exceeding 1 mm. Accordingly, as in the case of separating particles with sieves, it is requisite to first capture and remove large aggregates with a filter having a large pore size, and then to remove smaller aggregates by the use of filters having stepwise decreasing pore sizes. Some of the leukocytes may rather secondarily be captured by a prefilter at its layer having the smallest pore size, which layer is to be utilized to remove small aggregates. However, the proportion of such captured leukocytes is extremely small. Essentially, the removal of leukocytes must be effected by the use of a main filter as described below.

Leukocytes as the principal matter to be removed according to the present invention have a diameter of from 5 to 20 μm, and their sizes are much more uniform than those of aggregates. It is believed that the removal of leukocytes by a filter is due to the adsorption thereof onto the fibers contained in the filter. The present inventors previously found that the concentration of leukocytes passing through a fiber laminate decreases in exponential relationship with the thickness of the fiber laminate (Japanese Patent Application No. 1-296269). This suggests that leukocytes are adsorbed with a certain probability onto fibers at every contact of leukocytes with fibers around their crossover points during the flow of leukocytes through the fiber laminate in the direction of the thickness of the fiber laminate, and hence supports the above belief that the removal of leukocytes by a filter is due to the adsorption thereof onto the fibers.

The terminology "crossover point" used herein is defined below. That is, in a filter element comprised of a large number of fibers, the "crossover point" refers to points where at least two fibers are engaged with each other in a crossing relationship, points where at least two fibers are engaged with each other in a grade separation relationship with a minor spacing therebetween which is smaller than the diameter of each leukocyte, and points where at least two fibers are engaged with each other in an adjacent relationship with an inter-fiber spacing therebetween which is smaller than the diameter of each leukocyte.

Accordingly, the conventional investigations on a main filter as a member of a filter for removing leukocytes have been focused on increasing the above adsorption probability, i.e., decreasing an average fiber diameter, increasing a packing density, and the like.

On the other hand, in H. Prins; use of microfiber nonwovens in blood filtration, Session Applications 1-Filtration & Separation, Index 90 Congress, N.P.B.I., The Netherlands, it is described that among leukocytes, granulocytes are removed by adhesion and lymphocytes are removed by sieving mechanism so that it is necessary to employ functionally different filter elements, one being adapted for granulocytes and the other being adapted for lymphocytes. Further, it is described that a filter element having an average fiber diameter of 5 μm was used for the removal of granulocytes while a filter element having an average fiber diameter of 2.5 μm was used for the removal of lymphocytes. However, the filter disclosed in this reference is of a large size, and no contemplation appears in the reference with respect to improvement of the performance of the filter, e.g., removal of leukocytes to a level of $10^{-4}$ or less in terms of a final leukocyte residual ratio. Actually, the filter element having an average fiber diameter of 5 μm corresponds to the above-mentioned prefilter. Although this filter element removes a portion of leukocytes, the primary function thereof is to remove small aggregates as described in the reference as well. On the other hand, the filter element having an average fiber diameter of 2.5 μm which is used for removing lymphocytes, also removes a large proportion of granulocytes, and this filter element corresponds to the above-mentioned conventional main filter. Accordingly, no problem is posed even if both granulocytes and lymphocytes are removed by a filter element having an average fiber diameter of 2.5 μm without the removing of granulocytes by a filter element having an average fiber diameter of 5 μm. That is, the filter element having an average fiber diameter of 5 μm is not considered as an element which is indispensable for the removal of leukocytes. Actually, in the reference, no contemplation is made with respect to the necessity to remove granulocytes by means of a filter element having an average fiber diameter of 5 μm prior to the use of a filter element having an average fiber diameter of 2.5 μm.

Moreover, the filter element having an average fiber diameter of 2.5 μm corresponds to the conventional main filter as mentioned above, and hence a high leukocyte removal efficiency cannot be expected with respect to this type of filter element.

Illustratively stated, in the reference, there is neither intention to remove granulocytes by means of a filter element having an average fiber diameter of 5 μm (which can be regarded as a prefilter in the reference) prior to the filtration by the use of a filter element having an average fiber diameter of 2.5 μm (which can be regarded as a main filter in the reference), nor recognition of the necessity of the same.

Recently, in accordance with wider recognition of the importance of leukocyte-free blood transfusion, a filter for removing leukocytes which exhibits an improved leukocyte removal efficiency and has a smaller size and a smaller internal space volume, has been demanded in the art. Usually, a blood product remaining inside a filter after filtration operation to remove leukocytes is discarded together with the filter. Therefore, to minimize the waste of blood product, a filter having a small internal space volume is demanded. The terminology "internal space volume" used herein means the volume of the whole space inside a filter in which a filter element is placed, the whole space including the void portion of the filter element. With respect to the capability of removing leukocytes, even the most effective filter known in the art can remove leukocytes to a level of a leukocyte residual ratio of about $10^{-3}$ at the best, and further it cannot avoid the above-mentioned serious side effects. Generally, it is desired that the proportion of blood product discarded with a filter be limited to a level as low as 10–15% or less. For meeting this requirement, it is desired that the filter be of a small size such that it has an internal space volume as small as 35 ml or less per unit of whole blood or red cell product or as small as 20 ml or less per 5 units of platelet product. However, the conventional filters cannot simultaneously realize both high leukocyte removal efficiency and satisfactorily small internal space volume.

The measures for improving leukocyte removal efficiency which can readily be conceived by persons skilled in the art would be to increase the amount of main filter or to employ a filter element having a smaller average fiber diameter. For increasing the amount of main filter while keeping the internal space volume thereof at the above-mentioned value or less, it is necessary to increase the packing density of main filter in a container so as to suppress the internal space volume. Generally, the upper limit of the packing density is about 0.4 g/cm³. At a higher packing density, it is difficult to accomplish the packing in a container due to the repulsive force of non-woven fabric. To avoid this difficulty, heat pressing or the like may be performed for the non-woven fabric. However, this results in a collapse of the non-woven fabric into a film, which can no longer function as a filter. Therefore, for improving leukocyte removal efficiency, it is necessary to adopt a method in which the amount of main filter is increased while keeping the packing density at 0.4 g/cm³ or less, or a method in which a main filter having a smaller average fiber diameter is used (as a result of the studies of the present inventors, it has been found that in order to attain a leukocyte residual ratio of $10^{-4}$ or less while keeping the packing density at a value within the above-mentioned range, the average fiber diameter of non-woven fabric must be 1.6 μm or less).

In either method, however, there has been a problem that the improvement of the capability of leukocyte removal is inevitably accompanied by an increase of a pressure loss in a main filter region during the passage of a blood product so that filtering speed is drastically lowered before the completion of filtration of a predetermined amount of blood.

As mentioned hereinbefore, according to the finding of the present inventors, the concentration of leukocytes passing a fiber laminate is decreased in an exponential relationship with the thickness of the fiber laminate in the passage of a blood product through the fiber laminate. Further, it has been found that the smaller the average fiber diameter and the higher the packing density, the greater the degree of this decrease. Accordingly, an increase in the capability of leukocyte removal with an internal space volume limited to within the above-mentioned range may be performed by employing fibers having a small average diameter or increasing a packing density in a main filter. However, these measures are inevitably accompanied by serious problems, as mentioned hereinbefore. That is, when these measures are actually adopted in order to improve a leukocyte residual ratio to $10^{-4}$ or less, the leukocyte-removing ability is improved but a pressure loss is increased in a main filter region during the passage of a blood product with the improvement of the capability of the main filter to remove leukocytes, so that filtering speed is drastically lowered before the completion of filtration of a predetermined amount of blood. With a view toward elucidating the reason for the problems, the present inventors have made intensive studies with respect to the factors increasing the pressure loss of a filter. As a result, it has unexpectedly been found that the major reason for the problems is a clogging of the filter with leukocytes.

Before the present invention, it has generally been believed that the pressure loss of a filter is essentially attributed to a viscous resistance of blood passing through the filter, and that the voids of the filter through which blood can flow are clogged with aggregates and thus an increase in pressure loss accompanying blood filtration occurs due to an increase in linear velocity of blood in the remaining unclogged portions. Further, it has been known since the time a flocculent fiber mass was used in a leukocyte-removing filter that blood flow rate is drastically lowered when fibers having a small average fiber diameter are employed and that the same occurs when packing density is increased. In such a case, however, blood flow rate is low from the initial stage of blood filtration. This is a phenomenon which is clearly different from the problem of flow rate being rapidly lowered from the middle of blood filtration as currently encountered by the present inventors. That is, the problem is attributed to a sharp increase in viscous resistance of blood which is caused by effecting a diameter minimization and a packing density increase for a flocculent fiber mass. This problem has been solved by the use of a non-woven fabric as a filter material, as disclosed in Japanese Patent Application Publication Specification No. 2-13587.

In fact, the degree of viscous resistance of blood has never become a problem with respect to the conventional leukocyte-removing filters comprised of a non-woven fabric, which filters can remove leukocytes to a level of a leukocyte residual ratio of about $10^{-3}$ or so. Problems relating to pressure loss or flow rate, if any, have been concerned with clogging of the filter with aggregates which increased during the storage of blood, especially in the case of filtration of old blood which has been stored for a prolonged period of time, which clogging causes a pressure loss increase and a filtration speed lowering from the middle of blood filtration. These problems have also been solved by employing a prefilter for removal of aggregates as disclosed in Japanese Patent Application Publication Specification No. 2-13588, and such filters have conventionally been widely utilized in the art.

DISCLOSURE OF THE INVENTION

The problem which the inventors have had to solve is one which has been encountered for the first time in an attempt to improve the leukocyte removal to a level of a leukocyte residual ratio to $10^{-4}$ or less. And, the real situations underlying the problem have been elucidated after it became feasible to measure an extremely low concentration of leukocytes, such as $10^{-4}$ or less in terms of leukocyte residual ratio and after it became apparent that leukocyte concentrations are decreased in an exponential relationship with the thickness of a fiber laminate. That is, as long as use is made of the conventional filters comprised of a main filter of about 1.7 to 3.0 μm which exhibit a leukocyte removal ratio of about $10^{-3}$ or so in terms of a leukocyte residual ratio, an increase in pressure loss attributed to clogging of the filter with leukocytes cannot be found at all and hence no anticipation has been made of the occurrence of the problem.

During the investigations toward the present invention, using various non-woven fabrics having different average fiber diameters, the present inventors studied factors to be generally considered in designing a leukocyte-removing filter, such as packing density of a non-woven fabric and cross-sectional area and thickness of a filter. The studies showed that as long as use was made of a single main filter, the above-mentioned problem was not solved. Then, careful observations have been made, under various conditions, with respect to behavior of leukocyte concentration decrease in relation to the thickness of a main filter and with respect to the behavior of pressure loss in relation to the amount of filtered blood. As a result, surprisingly, it has become apparent that an increase in pressure loss is caused by an adsorption of leukocytes onto the most upstream portion of a main filter, which adsorption narrows the voids of the main filter.

As mentioned above, the number of leukocytes which pass through a main filter is decreased in an exponential relationship with the thickness of the main filter. Accordingly, at a portion of the filter which is nearer to the extreme upstream portion (where first contact is made with a blood product), the amount of leukocytes adsorbed thereon becomes greater. Therefore, when the packing density of a main filter is increased by increasing the amount of fibers followed by compression, the resultant filter having its void ratio decreased by compression adsorbs leukocytes in an amount which is the same or more as compared to that attained by the filter before the compression, thereby causing a clogging of the main filter by leukocytes to be markedly increased around the upstream surface of the filter as compared to that experienced by the filter before the compression. This is believed to bring about a marked increase in pressure loss. When a main filter having a small average fiber diameter is used, the voids thereof are inherently so small that the resistance to blood passage is high and the capability of leukocyte removal is high per unit thickness, leading to a high degree of clogging of the filter with leukocytes and a marked increase in pressure loss. This is a phenomenon clearly observed for the first time when it is intended to increase the capability of leukocyte removal to a certain level or higher in the case where packing density is increased or a non-woven fabric having a small average fiber diameter is used in an effort to enhance the capability of leukocyte removal. This is a phenomenon not observed with respect to the conventional filters having a relatively large average fiber diameter (1.7 to 3.0 μm) and a low packing density (about 0.2 g/cm³ or lower), which have been designed so as to remove leukocytes to a level of a leukocyte residual ratio of about $10^{-3}$ or so.

The substance of the above-mentioned problems resides in that leukocyte adsorption is concentrated at an upstream region, especially at the most upstream layer, of a main filter having a high packing density and a small average fiber diameter, these being inevitable for high performance.

The present inventors have made extensive and intensive studies with a view toward solving the above-mentioned problems. As a result, it has been found that a blood product having an extremely low leukocyte residual ratio can be obtained, without suffering from a clogging of a leukocyte-removing filter, by subjecting a blood product to be filtered to a first stage leukocyte-removing treatment to remove at least 60% of all leukocytes contained in the blood product, thereby obtaining a leukocyte-depleted blood product, and then subjecting the leukocyte-depleted blood product to a second stage leukocyte-removing treatment through a microfilter element comprised of a non-woven or a woven fabric having a small average fiber diameter. In the above-mentioned first stage leukocyte-removing treatment, a centrifuge or the conventional leukocyte-removing filters can be employed. However, it has been found that a leukocyte-removing filter system which can exert a high leukocyte-removing efficiency and/or can realize an extremely small sized leukocyte-removing apparatus, can be obtained by using a filter comprised of a non-woven or a woven fabric in the first stage leukocyte-removing treatment and using, in combination therewith, the above-mentioned microfilter element in the second stage leukocyte-removing treatment. The present invention has been completed on the basis of these findings.

Accordingly, it is an object of the present invention to provide a method for removing leukocytes from a leukocyte-containing blood product to a level of a leukocyte residual ratio of $10^{-4}$ or less.

It is another object of the present invention to provide a filter system which can realize a leukocyte-removing filter exhibiting a leukocyte-removing efficiency as excellent as $10^{-4}$ or less in terms of leukocyte residual ratio in which allosensitization can be prevented, which leukocyte-removing filter has a size as small as 35ml or less in terms of the internal space volume of a filter per unit of whole blood or a red cell product when the filter is intended to be used for treating whole blood or a red cell product, or 20 ml or less in terms of the internal space volume of a filter per 5 units of a platelet product when the filter is intended to be used for treating a platelet product in order to keep the amount of blood product discarded with a filter at a level as low as 10–15% or less.

It is a further object of the present invention to provide a filter system which can realize a marked miniaturization of the conventional leukocyte-removing filters exhibiting a leukocyte residual ratio of from $10^{-2}$ to $10^{-3}$ which is on a currently prevailing level.

Accordingly, in one aspect of the present invention, a method for removing leukocytes from a leukocyte-containing blood product is provided, which comprises:

subjecting a leukocyte-containing blood product to a first stage leukocyte-removing treatment to remove at least 60% of all leukocytes contained in the leukocyte-containing blood product, thereby obtaining a leukocyte-depleted blood product; and passing the leukocyte-depleted blood product through a microfilter element to perform a second stage leukocyte-removing treatment, the microfilter element comprising a non-woven or a woven fabric comprised of fibers having an average diameter of from 0.3 to 1.6 μm.

A centrifuge or the conventional leukocyte-removing filters may be employed in the first stage leukocyte-removing treatment to remove at least 60% of all leukocytes according to the method of the present invention. On the other hand, the microfilter element for use in the second stage leukocyte-removing treatment is comprised of fibers having an average diameter of from 0.3 to 1.6 μm.

Leukocyte-containing blood products to be treated by the method of the present invention include whole blood and red cell and platelet products obtained by separation of whole blood.

The microfilter element for use in the method of the present invention assumes a fiber cloth structure composed of a single or a plurality of fiber cloth layers comprised of a non-woven or a woven fabric, each of the plurality of fiber cloth layers having an average fiber diameter substantially identical with the average fiber diameter of all of the plurality of fiber cloth layers. The terminology "non-woven fabric" used herein defines a cloth-form fabric in which a mass of fibers or yarns are chemically, thermally or mechanically bonded without being sewn. In this connection, when fibers hold a certain shape by friction due to inter-fiber contacts or by entanglement thereof, the fibers are included in the category of mechanically bonded fibers. On the other hand, the terminology "woven fabric" used herein means a fabric in which warp and weft strands cross over, as generally defined.

In another aspect of the present invention, a filter system for removing leukocytes from a leukocyte-containing blood product is provided, which comprises:

(1) a first filter element comprising a non-woven or a woven fabric capable of removing at least 60% of all leukocytes contained in a red cell concentrate when the red cell concentrate is filtered through the first filter element, the red cell concentrate being obtained by adding CPD solution to whole blood in an effective anti-coagulative amount and removing plasma from 1 unit of the whole blood containing CPD solution until a hematocrit value of the resultant red cell concentrate becomes about 67%; and (2) a second filter element comprising a non-woven or a woven fabric comprised of fibers having an average diameter of from 0.3 to 1.6 μm, the second filter element being in communication with the first filter element, wherein an average diameter of fibers of the first filter element is larger than the average diameter of the fibers of the second filter element, and the first filter element is positioned upstream of the second filter element with respect to a direction in which a leukocyte-containing blood product to be treated for removal of leukocytes is adapted to flow.

The first filter element and the second filter element for use in the filter system of the present invention are each composed of a single or a plurality of fiber cloth layers comprised of a non-woven or a woven fabric, which plurality of fiber cloth layers each have an average fiber diameter substantially identical with the average fiber diameter of all of the plurality of fiber cloth layers, as in the above-mentioned microfilter element for use in the above-mentioned method for removing leukocytes according to the present invention. Also, the first filter element and the second filter element can assume a structure in which these are, respectively, constituted of an upstream portion and a downstream portion of an unseparable single layer.

The second filter element for use in the filter system of the present invention has the same construction as that of the microfilter element for use in the method for removing leukocytes according to the present invention. That is, as mentioned above, the second filter element has an average fiber diameter of from 0.3 to 1.6 μm, preferably from 0.5 to 1.4 μm. More specifically, the average fiber diameter of a second filter element for whole blood or a red cell product is preferably in the range of from 0.7 to 1.3 μm, more preferably from 0.7 to 1.7 μm. On the other hand, the average fiber diameter of a second filter element for a platelet product is preferably in the range of from 0.5 to 1.0 μm, more preferably from 0.5 to 0.8 μm.

Fibers having an average diameter of less than 0.3 μm are not suitable because it is difficult to stably manufacture a non-woven fabric therefrom and viscous resistance of blood becomes too high when the blood contacts a filter produced from such fibers. On the other hand, fibers having an average diameter of more than 1.6 μm are not suitable because a filter produced by the use of such fibers is not satisfactory as the second filter element for use in the filter system, of the present invention from the viewpoint of leukocyte removal efficiency, and because the desired internal space volume of a filter cannot be obtained unless the packing density is increased to greater than 0.4 g/cm$^3$.

The average fiber diameter of a filter element for use in the present invention refers to a value determined by the following method. A portion of a filter element is sampled, and the resultant sample is photographed using a scanning electron microscope. In the sampling, an effective filtering area portion of the filter element is partitioned into 0.5 cm×0.5 cm squares. From them, six squares are randomly sampled. In the random sampling, for example, an address is given to each of the above-mentioned square partitions, and appropriate square partitions are chosen, for example by a method in which the table of random numbers is used. With respect to each of the first sampled three square partitions, the center portion of the upstream side surface is photographed at a magnification of 2500. On the other hand, with respect to each of the remaining three square partitions, the center portion of the downstream side surface is photographed at the same magnification. During the photographing, a plurality of photographs are taken at the center portion and its neighborhood of each sampled square partition. Photographing is continued until the number of fibers appearing in the photographs exceeds 10, with the proviso that this number should be limited to a minimum. The diameter is measured of each of the fibers appearing in the photographs. The term "diameter" used herein means the width of a fiber as viewed in a direction perpendicular to the fiber axis. The average fiber diameter is the quotient of the sum of all measured fiber diameters divided by the number of fibers, provided that when a plurality of fibers overlap each other to thereby cause the measurement of the fiber width to impossible due to the shadowing of other fibers, when a plurality of fibers are formed into a thick fiber through melt adhesion of the like, or when fibers of markedly different diameters are mixed, measurement data are omitted. Further, when the average fiber diameters are clearly different between the upstream side and the downstream side of a filter element, it is not regarded as a single filter element. The terminology "clear difference in average fiber diameter" used herein means that a significant difference exists in the statistical sense between average fiber diameters. In the above case, the upstream side and the downstream side are regarded as constituting different filter elements. A boundary is determined between the upstream side and the downstream side, and subsequently the average fiber diameters are separately measured for both of them.

In the leukocyte-removing method and the leukocyte-removing filter system according to the present invention, it is requisite that at least 60% of all leukocytes contained in a blood product to be treated be removed prior to treatment by a second filter element. Preferably from 60 to 99%, more preferably from 80 to 99% of all leukocytes are removed. When the leukocyte removal ratio attained by a first filter element is less than 60%, a disadvantage occurs that clogging of a second filter element with leukocytes cannot be satisfactorily improved. That is, it is requisite that the first filter element be capable of removing at least 60% of all leukocytes contained in a red cell concentrate when the red cell concentrate is filtered through the first filter element, the red cell concentrate being obtained by adding CPD solution to whole blood in an effective anti-coagulative amount and removing plasma from 1 unit of the whole blood containing CPD solution until a hematocrit value of the resultant red cell concentrate becomes about 60%.

In the filter system of the present invention, it is requisite that the average diameter of fibers of the first filter element be larger than the average diameter of the fibers of the second filter element. It is preferred that the average diameter of the fibers of the first filter element be from 0.8 to 3.0 μm, and that the average diameter of the fibers of the first filter element be at least 1.2 times the average diameter of the fibers of the second filter element. It is more preferred that the average diameter of the fibers of the first filter element be from 1.0 to 2.0 μm. More specifically, the more preferred average fiber diameter is from 1.5 to 1.8 μm in a first filter element for use in the treatment of whole blood or a red cell product, and is from 1.0 to 1.5 μm in a first filter element for use in the treatment of a platelet product. When the ratio of the average fiber diameter of the first filter element to the average fiber diameter of the second filter element is lower than 1.2, a functional difference between the first filter element and the second filter element must be brought about only by a difference in packing density. This disadvantageously limits the scope of variation in design.

In the filter system of the present invention, the average pore size of the first filter element is preferably from 4 to 25 μm, more preferably from 6 to 20 μm. The average pore size of the second filter element is preferably from 2 to 18 μm, more preferably from 4 to 12 μm. The terminology "average pore size" used herein means the average pore size of the minimum unit (1 sheet) of a filter element which has not yet been housed in a container. This average pore size refers to MFP (Mean Flow Pore Size) measured by means of Coulter porometer II (Coulter Electronics and Limited, U.S.A.). The average pore size is an index which is seemingly related to the volume of interstices and the manner and degree of entanglement of fibers constituting a filter element. Although no satisfactorily theoretical support has been obtained and hence the cause is not elucidated, when the average pore size is outside the above-mentioned range, an appropriate balance between pressure loss and leukocyte removal efficiency is likely to be lost. Therefore, it is preferred that the average pore size be in the above-mentioned range.

It is requisite that the first and the second filter elements be so constructed as to allow a blood product to initially pass through the first filter element and then pass through the second filter element. In particular, the above filter elements may be separate filter layers, which are laminated to form a filter system. In another form, a single unseparable layer may be constituted of an upstream portion and a downstream portion which respectively satisfy the requirements for a first filter element and the requirements for a second filter element. In a further form, a filter may comprise at least three filter elements respectively having different average fiber diameters which are piled one upon another in the order of large average fiber diameter to small average fiber diameter from an upstream side to a downstream side. If any two of the above-mentioned filter elements satisfy the requirements defined in the present invention, these represent the first and the second filter elements for use in the present invention.

Moreover, in the filter system of the present invention, at least one conventional prefilter may be laminated on an upstream side of the main filter comprised of the above-mentioned first and second filter elements. Also, a third filter element, a fourth filter element and so on may be disposed on the downstream side of the second filter element in such an order that the average fiber diameter is decreased with the increase of filter element number on the condition that the average fiber diameter is in the range of from 0.3 to 1.6 μm.

In the leukocyte-removing method of the present invention, as mentioned above, the removal of at least 60% of all leukocytes may be performed by the use of a member selected from a centrifuge and the conventional leukocyte-removing filter, which may be incorporated in an apparatus for systemization. Further, the removal of at least 60% of all leukocytes may be attained by incorporating in a container a filter element capable of removing at least 60% of all leukocytes and comprised of fibers having an average fiber diameter larger than that of the second filter element.

As described above, the present invention provides a technique particularly advantageous for designing a miniaturized filter system exhibiting a high leukocyte removal efficiency, specifically a miniaturized filter system which exhibits a leukocyte removal efficiency as excellent as $10^{-4}$ or less in terms of leukocyte residual ratio at which allosensitization can be prevented, and which has an internal space volume of 35 ml or less per unit of whole blood or a red cell product or an internal space volume of 20 ml or less per 5 units of a platelet product in order to keep the amount of blood product discarded with a filter at a level as low as 10-15% or below. Nevertheless, the technique of the present invention can be applied to the conventional leukocyte-removing filters exhibiting a leukocyte residual ratio of about $10^{-2}$ to $10^{-3}$. In this case, a filter system which exhibits a pressure loss equivalent to the conventional level but has a smaller size, or a filter system which has substantially the same internal space volume as those of the conventional filter systems but exhibits a lower pressure, can be provided.

According to the present invention, with respect to a high performance leukocyte-removing filter system for whole blood or a red cell product which can remove leukocytes to a level of a leukocyte residual ratio of $10^{-4}$ or less, a miniaturized, high performance filter system having an internal space volume of from 15 to 35 ml per unit of whole blood or a red cell product and an effective filtration area of from 20 to 110 cm$^2$, preferably having an internal space volume of from 20 to 30 ml per unit defined above and an effective filtration area of from 25 to 95 cm$^2$, can be realized. On the other hand, with respect to a filter system of conventional type which can remove leukocytes to a level of a leukocyte residual ratio of about $10^{-2}$ to $10^{-3}$, a miniaturized filter system having an internal space volume of from 7 to 18 ml and an effective filtration area of from 10 to 65 cm$^2$, preferably having an internal space volume of from 7 to 15 ml and an effective filtration area of from 10 to 55 cm$^2$, more preferably having an internal space volume of from 10 to 15 ml and an effective filtration area of from 20 to 55 cm$^2$, can be realized by the present invention.

With respect to a high performance leukocyte-removing filter system for a platelet product which can remove leukocytes to a level of a leukocyte residual ratio of $10^{-4}$ or less, a miniaturized high performance filter system having an internal space volume of from 6 to 20 ml per 5 units of a platelet product and an effective filtration area of from 3 to 108 cm$^2$, preferably having an internal space volume of from 6 to 15 ml per 5 units defined above and an effective filtration area of from 3 to 81 cm$^2$, more preferably having an internal space volume of from 6 to 10 ml per 5 units defined above and an effective filtration area of from 5 to 54 cm$^2$, can be realized by the present invention. On the other hand, with respect to a filter system of conventional type which can remove leukocytes to a level of a leukocyte residual ratio of about $10^{-2}$ to $10^{-3}$, a miniaturized filter system having an internal space volume of from 3 to 8 ml and an effective filtration area of from 3 to 43 cm$^2$, preferably having an internal space volume of from 3 to 6 ml and an effective filtration area of from 5 to 32 cm$^2$, can be realized by the present invention.

When the internal space volume is smaller than each of the above-mentioned lower limits, unfavorably, a pressure loss is likely to increase and a filtration time is likely to be prolonged despite the effects of the present invention. On the other hand, when the internal space volume is larger than each of the above-mentioned upper limits, the amount of blood product discarded with a filter is unfavorably increased. When the effective filtration area is smaller than each of the above-mentioned lower limits, unfavorably, not only is a clogging of a second filter element with leukocytes increased to an extent which cannot be disregarded any more, but also viscous resistance of blood is increased with an increase in linear velocity during blood treatment. On the other hand, when the effective filtration area is larger than each of the above-mentioned upper limits, the thickness of a filter must be decreased to an extreme extent in order to keep the internal space volume thereof within the desired range, and under such a restraint, if the filter element is packed in an amount necessary for attaining the desired leukocyte removal efficiency, the packing density unfavorably becomes extremely high, leading to a difficulty in production.

The packing density of each of the first and second filter elements is preferably in the range of from 0.1 to 0.4 g/cm$^3$, more preferably from 0.15 to 0.38 g/cm$^3$. Especially, in the case of a second filter element, the still more preferred range is from 0.20 to 0.38 g/cm$^3$, and the most preferred range is from 0.25 to 0.38 g/cm$^3$. When the packing density is lower than 0.1 g/cm$^3$, unfavorably, the number of inter-fiber crossover points providing sites for adsorption of leukocytes becomes small, and handling characteristics and performance stability are not satisfactory. On the other hand, the reason for the unfavorableness of packing density of more than 0.4 g/cm$^3$ resides in difficulties in manufacturing, as mentioned above.

With respect to the second filter element, the A value defined below is preferably in the range of from 0.1 to 0.5, more preferably from 0.15 to 0.4, most preferably from 0.22 to 0.35.

The A value = packing density (g/cm$^3$)/average fiber diameter (μm)

When the A value is smaller than 0.1, unfavorably, leukocyte removal efficiency is likely to become poor. On the other hand, when the A value is larger than 0.4, unfavorably, viscous resistance of blood is likely to be high.

In the present invention, one unit of whole blood refers to 400-500 ml (the amount of blood defined by one unit of whole blood varies depending on the country, for example, 400 ml in Japan, 500 ml in Germany, and 450 ml in the United States and France) of collected blood having, added thereto, an anticoagulant, such as CPD solution, CPDA solution and ACD solution. One unit of a red cell product refers to a red cell concentrate prepared by removing a portion of plasma or a platelet-enriched plasma from one unit of whole blood, or a red cell concentrate having, added thereto, a red cell preservative, such as Adsol, Neutricel, SAGM and MAP. Five (5) units of a platelet product refers to an apheresis platelet product containing platelets in an amount of 5 times one unit of a platelet concentrate prepared from one unit of whole blood, or in an amount equivalent to the above-mentioned amount.

Each of the first and second filter elements for use in the filter system of the present invention may be preliminarily processed according to the conventional technique so as to have a predetermined thickness and a predetermined density before being housed in a container, or the first and second filter elements may be unified into an assembly of the individual elements by preliminary processing. Representative examples of filter element forms for use in the present invention include non-woven fabrics, such as a melt-blown non-woven fabric, a flash non-woven fabric, a spun bonded fabric, a spun laced non-woven fabric, a wet-type non-woven fabric, a dry-type non-woven fabric and a needle punched non-woven fabric, a paper, a woven fabric and a mesh. Representative examples of fiber materials include synthetic fibers, such as those of a polyamide, an aromatic polyamide, a polyester, polyacrylonitrile, polytrifluorochloroethylene, polymethyl methacrylate, polystyrene, polyethylene and polypropylene, and regenerated fibers, such as those of cellulose and cellulose acetate. In the present invention, in order to improve the leukocyte removal efficiency and, if desired, to improve the platelet removal efficiency of a filter element, a conventional surface modification may be effected (see The Role of Leukocyte Depletion in Blood Transfusion Practice, Proceedings of the International Workshop, London, Jul. 9, 1988, B. Brozovic, p. 38, Blackwell Scientific Publications, Oxford, London).

Also, in order to have leukocytes effectively adsorbed onto a filter element while allowing most of the platelets to pass therethrough, a conventional surface modification may be effected (see European Patent No. 0267286).

BEST MODE FOR CARRYING OUT THE INVENTION

Hereinbelow, the present invention will be illustrated in greater detail with reference to the following Examples. In the present invention, the terminology "packing density" of a filter element means a quotient of the weight of a filter element conditioned for service divided by the product of the effective filtration area multiplied by the thickness of the filter element, with respect to a predetermined portion of the effective filtration area. The terminology "internal space volume" of a filter used herein means a value determined by first injecting a liquid, such as water, physiological saline solution or an aqueous alcohol solution, into a filter through its inlet to thereby expel air from the inside of the filter, subsequently sealing the inlet and the outlet of the filter, and thereafter measuring the weight increase of the filter, followed by dividing this weight increase by the specific gravity of the injected liquid.

EXAMPLE 1

As a prefilter, two types of spun bonded non-woven fabrics respectively comprised of fibers having an average diameter of 32 μm and comprised of fibers having an average diameter of 13 μm were packed into a container having an effective filtration area of 67 mm × 67 mm so that the average packing density became 0.28 g/cm$^3$ and the total thickness became 1.1 mm. Then, as a first filter element of a main filter, a polyester melt-blown non-woven fabric comprised of fibers having an average diameter of 1.80 μm, which fabric had an average pore size of 10.2 μm, was packed into the above-mentioned container at a position downstream of the prefilter so that the packing density and thickness of the first filter element became 0.26 g/cm$^3$ and 3.0 mm, respectively. Further, as a second filter element, a polyester melt-blown non-woven fabric comprised of fibers having an average diameter of 1.23 μm, which fabric had an average pore size of 9.5 μm, was packed downstream of the first filter element so that the packing density and thickness of the second filter element became 0.32 g/cm$^3$ and 2.0 mm, respectively. Thus, a filter for removing leukocytes was prepared (the A value of the second filter element was 0.26). The thus obtained filter had an internal space volume of 32.4 ml and an effective filtration area of (6.7 cm)$^2$ = 44.9 cm$^2$.

513 ml of blood prepared by adding 63 ml of CPD solution to 450 ml of whole blood was subjected to centrifugation within 8 hours after collection of the whole blood to separate 243 ml of platelet-enriched plasma from the whole blood, thereby obtaining a red cell product. The red cell product was stored at 4° C. for 3 days, and a physiological saline solution was added thereto so that the volume became 360 ml (hematocrit: 63%). The red cell product was allowed to stand at room temperature (26° C.) until the temperature of the product reached 25° C. Then, the red cell product was filtered by the above-mentioned filter. The preparatory procedure before the filtration was performed by connecting the filter to a blood bag containing the red cell product through a blood circuit and applying pressure to the blood bag, thereby forcibly filling the filter with the blood. After filling the filter with the blood, the blood was caused to continuously flow at a constant rate of 15 ml/minute by means of PERISTA PUMP (manufactured and sold by ATTO Co., Japan) while measuring the pressure loss in the course of the filtration by means of a digital type pressure gauge. At the time when there was no longer blood in the blood bag, the filtration was completed, and the collection bag which had been connected to the downstream side of the filter through a blood circuit was cut off from the filter by cutting the blood circuit therebetween at a position 30 to 40 cm downstream of the blood outlet of the filter, thereby obtaining, as a collection liquid, the red cell product present in the collection bag and blood circuit.

The red cell product before filtration (hereinafter referred to as "pre-filtration liquid") and the collection liquid were measured with respect to the volume, the hematocrit and the number of leukocytes, thereby determining the red cell recovery and the leukocyte residual ratio.

Red Cell Recovery = [Collection Liquid Volume × Hematocrit (Collection Liquid)]/[Pre-filtration Liquid Volume × Hematocrit (Pre-filtration Liquid)].
Leukocyte Residual Ratio = [Number of Leukocytes (Collection Liquid)]/[Pre-filtration Liquid Volume × Leukocyte Concentration (Pre-filtration Liquid)].

With respect to the volumes of the pre-filtration liquid and the collection liquid, values obtained by dividing the weights of these liquids by 1.075 (a representative value of the specific gravity of a red cell product) were taken as the respective volumes. Further, the measurement of the leukocyte concentration of the pre-filtration liquid was performed by the following method.

The measurement of the leukocyte concentration of the pre-filtration liquid: A pre-filtration liquid diluted 10-fold with Türk's reagent was injected into a Burker-Türk type hemocytometer (manufactured and sold by Erma, Japan) and the leukocytes present in four major sections were counted through an optical microscope and the obtained number was taken as $n_{pre}$.

$$\text{Leukocyte Concentration} = n_{pre} \times (\tfrac{1}{4}) \times 10^5/\text{ml}.$$

The measurement of the number of leukocytes contained in a collection liquid was performed by the extremely sensitive method described below.

An EBSS solution (hereinafter referred to as "FICOLL solution") containing 5 % FICOLL 400 DL (manufactured and sold by Sigma Chemical Co., St. Louis, the U.S.A) was introduced into a bag containing a collection liquid while shaking to facilitate mixing, the EBSS solution having an equivolume relative to the volume of collection liquid. Then, the collection bag was fixed onto a plasma separation stand and allowed to stand still for 40 minutes After that period, a supernatant was gently collected without disturbing a precipitated layer of red cells. Then, FICOLL was again introduced into the collection bag in the same volume as employed above, and the same procedure as described above was repeated. The supernatant collected by the collecting operation thus conducted twice was divided into four centrifuge tubes each being CORNING 25350-250 (manufactured and sold by Corning Laboratory Science Company, New York, the U.S.A.) and centrifuged at 840×g for 15 minutes. Subsequently, the supernatant was discarded by means of an aspirator so carefully as not to withdraw the precipitate. 200 ml of a hemolysis solution (a 1.145% ammonium oxalate physiological saline solution) was introduced into each tube and the tubes were shaken to facilitate mixing, immediately followed by centrifugation at 468×g for 10 minutes. Subsequently, the supernatant was discarded by means of an aspirator while taking the same care as described above.

The precipitates in the four tubes were collected into a 15 ml centrifuge tube and a hemolysis solution was added thereto so that the total volume became 15 ml. The tube was allowed to stand still at room temperature for 10 minutes and then centrifuged at 468×g for 10 minutes. Part of the supernatant was carefully discarded so that the volume of the contents including the precipitates became 0.5 ml. The liquid in the tube containing the precipitates was stirred well to obtain a single cell suspension, and 50 μl of a fluorescent dyeing solution [69.9 mg/l Acridine Orange (manufactured and sold by Nacalai Tesque Inc., Japan)] was added, followed by stirring. The resultant liquid was injected into six hemocytometers of improved Neubauer type (manufactured and sold by Reichert Co., Buffalo, the U.S.A.) and the leukocytes present in 108 major sections were counted through an epi-fluorescence microscope (manufactured and sold by Nicon Corp., Japan).

From the resultant count ($n_{post}$) of leukocytes, the number of leukocytes (collection liquid) was calculated.

$$\textit{Number of Leukocytes (Collection Liquid)} = \underline{n_{post} \times (1/108) \times 10^4} \times 0.55 \times (1/0.55).$$

The underlined portion in the formula represents the leukocyte concentration (cells/ml) in the liquid (hereinafter referred to as "concentrate") obtained by concentrating the collection liquid using a FICOLL solution to a total volume of 0.55 ml. The leukocyte concentration is multiplied by the volume of the concentrate (0.55 ml) to obtain the number of leukocytes. The reason why the thus obtained number of leukocytes is further divided by 0.55 is that the recovery of leukocytes attained by means of a FICOLL solution is 55%.

As a result of the above calculations, it was found that the leukocyte residual ratio was $10^{-4.5}$, the pressure loss at the time of completion of the filtration was 75 mmHg and the red cell recovery was 90.2%.

The leukocyte removal ratio of the first filter element was 97.6%. Since the leukocyte concentration after the filtration by the first filter element was relatively high, measurement of the leukocyte concentration before and after the filtration by the first filter element was conducted by the method described above under the item "The measurement of the leukocyte concentration of the pre-filtration liquid".

COMPARATIVE EXAMPLE 1

An experiment was conducted under substantially the same conditions as in Example 1 except that as a main filter, only a polyester melt-blown non-woven fabric comprised of fibers having an average diameter of 1.80 μm was packed into the container so that the packing density and thickness became 0.40 g/cm$^3$ and 5.0 mm, respectively. The thus obtained filter had an internal space volume of 30.0 ml. As a result of the experiment, the leukocyte residual ratio was $10^{-3.8}$, the pressure loss at the time of completion of the filtration was 77 mmHg and the red cell recovery was 90.3%.

COMPARATIVE EXAMPLE 2

An experiment was conducted under substantially the same conditions as in Example 1 except that as a main filter, only a polyester melt-blown non-woven fabric comprised of fibers having an average diameter of 1.23 μm was packed into the container so that the packing density and thickness became 0.23 g/cm$^3$ and 5.0 mm, respectively. The thus obtained filter had an internal space volume of 32.2 ml. Results of the experiment showed that the leukocyte residual ratio was $10^{-4.4}$, the pressure loss at the time of completion of the filtration was 147 mmHg and the red cell recovery was 90.1%.

EXAMPLE 2

As a prefilter, two types of spun bonded non-woven fabrics respectively comprised of fibers having an average diameter of 32 μm and comprised of fibers having an average diameter of 13 μm were packed into a container having an effective filtration area of 67 mm ×67 mm so that the average packing density became 0.30 g/cm$^3$ and the total thickness became 1.1 mm. Then, as a first filter element of a main filter, a polyester melt-blown non-woven fabric comprised of fibers having an average diameter of 1.75 μm, which fabric had an average pore size of 13.7 μm, was packed into the above-mentioned container at a position downstream of the prefilter so that the packing density and thickness of the first filter element became 0.17 g/cm$^3$ and 0.8 mm, respectively. Further, as a second filter element, a polyester melt-blown non-woven fabric comprised of fibers having an average diameter of 1.23 μm, which fabric had an average pore size of 10.4 μm, was packed downstream of the first filter element so that the packing density and thickness of the second filter element became 0.27 g/cm$^3$ and 4.2 mm, respectively. Thus, a filter for removing leukocytes was prepared (the A value of the second filter was 0.22). The thus obtained filter had an internal space volume of 32.3 ml and an effective filtration area of (6.7 cm)$^2$=44.9 cm$^2$. 456 ml of blood prepared by adding 56 ml of CPD solution to 400 ml of whole blood was subjected to centrifugation within 8 hours after collection of the whole blood to separate 200 ml of platelet-enriched plasma from the whole blood, thereby obtaining a red cell concentrate. The red cell concentrate was stored at 4° C. for 3 days (hematocrit: 67%). The red cell concentrate was then allowed to stand at room temperature (26° C.) until the temperature of the concentrate reached 25° C. Then, the red cell concentrate was filtered by the above-mentioned filter. The preparatory procedure before the filtration was performed by connecting the filter to a blood bag containing the red cell concentrate through a blood circuit and applying pressure to the blood bag, thereby forcibly filling the filter with the blood. After filling the filter with the blood, the filtration was performed with a head of 1.5 m. At the time when there was no longer blood in the blood bag, the filtration was completed, and the collection bag which was connected to the downstream side of the filter through a blood circuit was cut off from the filter by cutting the blood circuit therebetween at a position 30 to 40 cm downstream of the blood outlet of the filter, thereby obtaining, as a collection liquid, the red cell product present in the collection bag and blood circuit.

The red cell recovery and the leukocyte residual ratio were determined in substantially the same manner as in Example 1.

As a result, the leukocyte residual ratio was $10^{-4.7}$, the filtration time was 31 minutes and the red cell recovery was 91.0%.

The leukocyte removal ratio of the first filter element of the main filter was 62.0%.

EXAMPLE 3

As a prefilter, two types of spun bonded non-woven fabrics respectively comprised of fibers having an average diameter of 32 μm and comprised of fibers having an average diameter of 13 μm were packed into a container having an effective filtration area of 90 mm ×90 mm so that the average packing density became 0.4 g/cm$^3$ and the total thickness became 0.7 mm. Further, as an additional prefilter, two types of fabrics, i.e., Paneron PF 860 (manufactured and sold by Dainic Co., Japan; average fiber diameter 12 μm) and a spun laced non-woven fabric comprised of fibers having an average diameter of 4.1 μm were also packed into the same container so that the average packing density became 0.30 g/cm$^3$ and the total thickness became 0.5 mm. Then, as a first filter element of a main filter, a polyester melt-blown non-woven fabric comprised of fibers having an average diameter of 1.75 μm, which fabric had an average pore size of 14.0 μm, was packed into the above-mentioned container at a position downstream of the prefilter so that the packing density and thickness of the first filter element became 0.38 g/cm$^3$ and 0.7 mm, respectively. Further, as a second filter element, a polyester melt-blown non-woven fabric comprised of fibers having an average diameter of 1.23 μm, which fabric had an average pore size of 10.5 μm, was packed downstream of the first filter element so that the packing density and thickness of the second filter element became 0.38 g/cm$^3$ and 2.5 mm, respectively. Thus, a filter for removing leukocytes was prepared (the A value of the second filter was 0.31). The thus obtained filter had an internal space volume of 52.0 ml and an effective filtration area of (9.0 cm)$^2$=81.0 cm$^2$.

456 ml of blood prepared by adding 56 ml of CPD solution to 400 ml of whole blood was subjected to centrifugation within 8 hours after collection of the whole blood to separate 200 ml of platelet-enriched plasma from the whole blood, thereby obtaining a red cell concentrate. The red cell concentrate was stored at 4° C. for 14 days (hematocrit: 67%). The red cell concentrate was allowed to stand at room temperature (26° C.) until the temperature of the concentrate reached 25° C. Then, after 2 units of the red cell concentrate were collected in a 200 ml blood bag, the red cell concentrate was filtered by the above-mentioned filter. The experiment was conducted in substantially the same manner as in Example 2 except that the filtration was performed with a head of 1.2 m.

Results showed that the leukocyte residual ratio was $10^{-4.2}$, the filtration time was 54 minutes and the red cell recovery was 89.4%.

The leukocyte removal ratio of the first filter element of the main filter was 81.8%.

EXAMPLE 4

As a prefilter, two types of spun bonded non-woven fabrics respectively comprised of fibers having an average diameter of 32 μm and comprised of fibers having an average diameter of 13 μm were packed into a container having an effective filtration area of 67 mm ×67 mm so that the average packing density became 0.47 g/cm$^3$ and the total thickness became 0.6 mm. Further, as a prefilter, two types of fabrics, i.e., Paneron PF 860 (manufactured and sold by Dainic Co., Japan; average fiber diameter: 12 μm) and a spun laced non-woven fabric comprised of fibers having an average diameter of 4.1 μm were packed into the container so that the average packing density became 0.375 g/cm$^3$ and the total thickness became 0.4 mm. Then, as a first filter element of a main filter, a polyester melt-blown non-woven fabric comprised of fibers having an average diameter of 1.68 μm, which fabric had an average pore size of 13.3 μm, was packed into the above-mentioned container at a position downstream of the prefilter so that the packing density and thickness of the first filter element became 0.33 g/cm³ and 1.2 mm, respectively. Further, as a second filter element, a polyester melt-blown non-woven fabric comprised of fibers having an average diameter of 0.89 μm, which fabric had an average pore size of 8.1 μm, was packed downstream the first filter element so that the packing density and thickness of the second filter element became 0.30 g/cm³ and 2.3 mm, respectively. Thus, a filter for removing leukocytes was prepared. The thus obtained filter had an internal space volume of 24.3 ml and an effective filtration area of (6.7 cm)² = 44.9 cm².

456 ml of blood prepared by adding 56 ml of CPD to 400 ml of whole blood was subjected to centrifugation within 8 hours after collection of the whole blood to separate 200 ml of platelet-enriched plasma from the whole blood, thereby obtaining a red cell concentrate. The red cell concentrate (hematocrit: 68%) was stored at 4° C. for 12 days. The red cell concentrate was then allowed to stand at room temperature (26° C.) until the temperature of the concentrate reached 25° C. Then, the red cell concentrate was filtered by the above-mentioned filter. The experiment was conducted in substantially the same manner as in Example 2 except that the filtration was performed with a head of 1.2 m.

Results showed that the leukocyte residual ratio was $10^{-4.3}$, the filtration time was 48 minutes and the red cell recovery was 90.0%.

The leukocyte removal ratio of the first filter element of the main filter was 85.2%.

EXAMPLE 5

As a prefilter, two types of spun bonded non-woven fabrics respectively comprised of fibers having an average diameter of 32 μm and comprised of fibers having an average diameter of 13 μm were packed into a container having an effective filtration area of 47 mm ×47 mm so that the average packing density became 0.24 g/cm³ and the total thickness became 2.2 mm. Then, as a first filter element of a main filter, a polyester melt-blown non-woven fabric comprised of fibers having an average diameter of 1.80 μm, which fabric had an average pore size of 12.8 μm, was packed into the above-mentioned container at a position downstream of the prefilter so that the packing density and thickness of the first filter element became 0.20 g/cm³ and 2.0 mm, respectively. Further, as a second filter element, a polyester melt-blown non-woven fabric comprised of fibers having an average diameter of 1.23 μm, which fabric had an average pore size of 10.2 μm, was packed downstream of the first filter element so that the packing density and thickness of the second filter element became 0.20 g/cm³ and 2.0 mm, respectively. Thus, a filter for removing leukocytes was prepared (the A value of the second filter was 0.16). The thus obtained filter had an internal space volume of 15.8 ml and an effective filtration area of (4.7 cm)² = 22.1 cm².

513 ml of blood prepared by adding 63 ml of CPD to 450 ml of whole blood was subjected to centrifugation within 8 hours after collection of the whole blood to separate 243 ml of platelet-enriched plasma from the whole blood, thereby obtaining a red cell product. The red cell product was stored at 4° C. for 10 days, and a physiological saline solution was added thereto so that the volume became 360 ml (hematocrit: 63%). The red cell product was allowed to stand at room temperature (26° C.) until the temperature of the product reached 25° C. Then, the red cell product was filtered by the above-mentioned filter. The experiment was conducted in substantially the same manner as in Example 2 except that the number of leukocytes contained in the collection liquid was determined by the following method.

Leukocyte concentration: 200 μl of a hemolysis solution and 30 μl of a fluorescent dyeing solution were added to 100 μl of the collection liquid, followed by stirring. The resultant liquid was injected into one to three hemocytometers of improved Neubauer type (manufactured and sold by Reichert Co., Buffalo, the U.S.A.) and the leukocytes present in 4 to 54 major sections were counted through an epifluorescent microscope (manufactured and sold by Nicon Corp., Japan). The obtained value was taken as $n_{post}'$.

Leukocyte Concentration (Collection Liquid) = $n_{post}'$ × (1/number of sections with respect to which leukocytes were counted) × (1/3.3) × $10^4$ cells/ml.
Number of Leukocytes = Volume of Collection Liquid × Leukocyte Concentration (Collection Liquid).

Results showed that the leukocyte residual ratio was $10^{-2.5}$, the filtration time was 15.2 minutes and the red cell recovery was 91.4%.

The leukocyte removal ratio of the first filter element of the main filter was 84.5%.

COMPARATIVE EXAMPLE 3

An experiment was conducted under substantially the same conditions as in Example 4 except that as a main filter, only a polyester melt-blown non-woven fabric comprised of fibers having an average diameter of 1.80 μm was packed so that the packing density and thickness of the fabric became 0.23 g/cm³ and 4.0 mm, respectively. The thus obtained filter had an internal space volume of 15.5 ml. As a result of the experiment, it was found that the leukocyte residual ratio was $10^{-1.9}$, the filtration time was 16.4 minutes and the red cell recovery was 92.0%.

COMPARATIVE EXAMPLE 4

An experiment was conducted under substantially the same conditions as in Example 4 except that as a main filter, only a polyester melt-blown non-woven fabric comprised of fibers having an average diameter of 1.23 μm was packed so that the packing density and thickness of the fabric became 0.17 g/cm³ and 4.0 mm, respectively. The thus obtained filter had an internal space volume of 15.8 ml. As a result of the experiment, it was found that the leukocyte residual ratio was $10^{-2.4}$, the filtration time was 24.3 minutes and the red cell recovery was 91.5%.

EXAMPLE 6

As a prefilter, a spun bonded non-woven fabric comprised of fibers having an average diameter of 13 μm was packed into a container having an effective filtration area of 30 mm×30 mm=9.0 cm² so that the average packing density and the thickness became 0.28 g/cm³ and 2.8 mm, respectively. Further as another prefilter, a spun laced non-woven fabric comprised of fibers having an average diameter of 4.1 μm was packed into the above-mentioned container so that the average packing density and thickness became 0.28 g/cm³ and 1.6 mm, respectively. Then, as a first filter element of a main filter, a melt blown non-woven fabric comprised of fibers having an average diameter of 1.23 μm was packed into the same container so that the average packing density and thickness became 0.20 g/cm³ (the average pore size: 10.2 μm) and 4.6 mm, respectively, and as a second filter element of a main filter, a melt blown non-woven fabric comprised of fibers having an average diameter of 0.72 μm was packed so that the average packing density and the thickness became 0.28 g/cm³ (the average pore size: 9.6 μm, the A value: 0.39) and 3.0 mm, respectively. These non-woven fabrics were packed in this order from the upstream side to the downstream side.

In the meantime, a copolymer comprised of 2-hydroxyethyl methacrylate and dimethylaminoethyl methacrylate in a molar ratio of 97:3 (hereinafter referred to simply as "HM-3") was synthesized by the conventional radical solution polymerization technique. The polymerization reaction was conducted at 60° C. for 8 hours with a total monomer concentration in ethanol of 1.0 mole/liter and in the presence of 1/200 mole/liter of azobisisobutylonitrile as an initiator. The resultant HM-3 was dissolved in ethanol at 40° C. so that the concentration became 1.0% and then, the resultant solution was passed through the container packed with the above-mentioned non-woven fabrics, followed by drying while introducing dry nitrogen thereto. Further, the resultant was satisfactorily dried at a temperature in the range of from 40 to 120° C. under vacuum for 4 hours to thereby coat the surface of the fibers of the non-woven fabric with HM-3, thus preparing a leukocyte-removing filter for platelet products. The internal space volume of the thus obtained filter was 11.0 ml.

10 units of platelet concentration liquid (preserved for 4 days) obtained from the Japanese Red Cross Society was filtered through the above-mentioned filter at room temperature with a head of 1.2 m. The filtration time was 28 minutes.

Platelet recovery and leukocyte residual ratio were obtained by the following formulae.

Platelet Recovery (%) = [{(Post-filtration Platelet Concentration) × (Post-filtration Liquid Volume)}/{(Pre-filtration Platelet Concentration) × (Pre-filtration Liquid Volume)}] × 100
Leukocyte Residual Ratio (%) = [(Post-filtration Leukocyte Concentration) × (Post-filtration Liquid Volume)]/[(Pre-filtration Leukocyte Concentration) × (Pre-filtration Liquid Volume)]

The platelet concentration before and after filtration and the leukocyte concentration before filtration were measured by means of an automatic corpuscle counter (Symex MICROCELL-COUNTER F-800, TOA Medical Electronics Co., Ltd., Japan), and the leukocyte concentration after filtration was measured by Cytospin Technique developed by Takahashi et al (Japanese Journal of Transfusion Medicine 35, No. 5, Pages 497 to 503, 1989). With respect to the volumes before and after the filtration, values obtained by dividing the weights of these liquids by a specific gravity value of 1.025 were taken as the volumes.

As a result, it was found that the platelet recovery was 89.6% and the leukocyte residual ratio was $10^{-4.6}$. The leukocyte recovery [{1-(leukocyte residual ratio)} × 100] of the first filter element of the main filter was 87.3%.

INDUSTRIAL APPLICABILITY

According to the method for removing leukocytes and the filter system for removing leukocytes of the present invention, leukocytes can be removed not only with a high leukocyte removal ratio represented by a leukocyte residual ratio of $10^{-4}$ which is extremely significant from the clinical point of view but also with a red cell recovery or platelet recovery as high as 85 to 90%, without suffering from a pressure loss and a considerable lowering of flow rate (which frequently accompanies the blood product treatment) at the time of filtration. Further, when the method and filter system of the present invention are applied to the common type leukocyte-removing filter capable of removing leukocytes to a level of a leukocyte residual ratio of from about $10^{-2}$ to $10^{-3}$, there can be provided a filter which is small in size with the same pressure loss as that of the conventional filter, or a filter which is small in pressure loss with the same internal space volume as that of the conventional filter.

We claim:

1. A method for removing leukocytes from a leukocyte-containing blood product by means of a filter system having an internal space volume of from 3 to 35 ml per unit of whole blood or a red cell product or per 5 units of a platelet product and an effective filtration area of from 3 to 110 cm², which comprises:

subjecting a leukocyte-containing blood product to a first stage leukocyte-removing treatment to remove at least 60% of all leukocytes contained in said leukocyte-containing blood product, thereby obtaining a leukocyte-depleted blood product; and passing said leukocyte-depleted blood product through a microfilter element to perform a second stage leukocyte-removing treatment, said microfilter element comprising a non-woven or a woven fabric comprised of fibers having an average diameter of from 0.3 to 1.6 μm.

wherein said first stage leukocyte-removing treatment comprises passing said leukocyte-containing blood product through a filter element comprising a non-woven or a woven fabric comprised of fibers having an average diameter which is from 0.8 to 2.0 μm and wherein said average diameter is at least 1.2 times the average diameter of the fibers of said microfilter element used in said second stage leukocyte-removing treatment.

2. The method of claim 1 wherein said average diameter of fibers of said first filter element is 1.0 to 2.0 μm.

3. A filter system for removing leukocytes from a leukocytes-containing blood product, comprising:

(1) a first filter element comprising a non-woven or a woven fabric capable of removing at least 60% of all leukocytes contained in a red cell concentrate when said red cell concentrate is filtered through said first filter element, said red cell concentrate being obtained by adding CPD solution to whole blood in an effective anti-coagulative amount and removing plasma from 1 unit of said whole blood containing CPD solution until a hematocrit value of the resultant red cell concentrate becomes about 67%; and (2) a second filter element comprising a non-woven or a woven fabric comprised of fibers having an average diameter of from 0.3 to 1.6 μm, said second filter element being in communication with said first filter element, wherein an average diameter of fibers of said first filter element is from 0.8 to 2 μm and said average diameter of the fibers of said first filter element is at least 1.2 times the average diameter of the fibers of said second filter element, and said first filter element is connected upstream of said second filter element with respect to a direction in which a leukocyte-containing blood product to be treated for removal of leukocytes is adapted to be flowed, said filter system having an inlet for a leukocyte-containing blood product and an outlet for a filtrate and having an internal space volume of from 3 to 35 ml per unit of whole blood or a red cell product or per 5 units of a platelet product and an effective filtration area of from 3 to 110 cm$^2$.

4. The filter system of claim 3, wherein said average diameter of fibers of said first filter element is 1.0 to 2.0 μm 5. The filter system according to claim 3, wherein said second filter element has an average pore size of from 2 to 18 μm.

6. The filter system according to claims 3 or 5, wherein said first filter element has an average pore size of from 4 to 25 μm.

7. The filter system according to claims 3 or 5, wherein said second filter element has an A value of from 0.15 to 0.4, said A value being defined as a ratio of a packing density (g/cm$^3$) of said second filter element to an average fiber diameter (μm) of said second filter element.

8. The filter system according to claim 6, wherein said second filter element has an A value of from 0.15 to 0.4, said A value being defined as a ratio of a packing density (g/cm$^3$) of said second filter element to an average fiber diameter (μm) of said second filter element.

9. A method for removing leukocytes from a leukocyte-containing blood product by means of a filter system having an internal space volume of from 3 to 35 ml per unit of whole blood or a red cell product or per 5 units of a platelet product and an effective filtration area of from 3 to 110 cm$^2$, which comprises:

subjecting a leukocyte-containing blood product to a first stage leukocyte-removing treatment to remove at least 60% of all leukocytes contained in said leukocyte-containing blood product, thereby obtaining a leukocyte-depleted blood product; and passing said leukocyte-depleted blood product through a microfilter element to perform a second stage leukocyte-removing treatment, said microfilter element comprising a non-woven or a woven fabric comprised of fibers having an average diameter of from 0.3 to 1.6 μm.

wherein said first stage leukocyte-removing treatment comprises subjecting said leukocyte-containing blood product to centrifugation, thereby separating said leukocyte-containing blood product into a leukocyte-enriched fraction and a leukocyte-depleted fraction and removing at least a part of said leukocyte-enriched fraction.

* * * * *